United States Patent [19]
Nohr et al.

[11] Patent Number: 5,618,614
[45] Date of Patent: Apr. 8, 1997

[54] MIXED SURFACTANT SYSTEM AS A DURABLE FABRIC COATING

[75] Inventors: Ronald S. Nohr, Roswell; John G. MacDonald, Decatur, both of Ga.

[73] Assignee: Kimberly-Clark Corporation, Neenah, Wis.

[21] Appl. No.: 398,333

[22] Filed: Mar. 3, 1995

Related U.S. Application Data

[62] Division of Ser. No. 174,734, Dec. 29, 1993, abandoned.
[51] Int. Cl.⁶ .................................................. B32B 7/00
[52] U.S. Cl. .......................... 442/118; 604/367; 604/370; 604/372
[58] Field of Search ................................. 428/289, 290, 428/272; 604/367, 370, 372

[56] References Cited

U.S. PATENT DOCUMENTS

| | | | |
|---|---|---|---|
| 4,426,333 | 1/1984 | Abel et al. | 8/138 |
| 5,057,361 | 10/1991 | Sayovitz et al. | 428/290 |
| 5,120,888 | 6/1992 | Nohr et al. | 524/99 |

*Primary Examiner*—Christopher Raimund
*Attorney, Agent, or Firm*—William E. Maycock

[57] ABSTRACT

A polymeric fabric treated with a composition for increasing the resistance to removal by an aqueous liquid of surfactants from the fabric. The fabric is made of fibers having a plurality of fiber-fiber interstices at junctions of two or more fibers. The composition includes water, a first surfactant, and a second surfactant which is structurally dissimilar to and less soluble in water than the first surfactant. One of the first and second surfactants has a solubility in water at 20° C. no greater than about 5 percent by weight, based on the weight of the water. The first and second surfactants are adapted to preferentially locate in the fiber-fiber interstices and resist removal therefrom by aqueous liquid. The preferential location of the surfactants in the fiber-fiber interstices of the fabric is accomplished by working the fabric after application of the composition to the fabric. The resulting fabric is wettable and demonstrates increased resistance to removal of surfactants by an aqueous liquid, compared to similar fabrics which have not been worked. The wettable fabrics are especially suited for incorporation in such disposable absorbent articles as diapers, feminine care products, such as sanitary napkins and tampons, incontinent care products, training pants, wipes, and the like.

21 Claims, 4 Drawing Sheets
(1 of 4 Drawing(s) in Color)

MIXED SURFACTANT SYSTEM AS A DURABLE FABRIC COATING

This application is a divisional of application Ser. No. 08/174,734 entitled "Mixed Surfactant System As A Durable Fabric Coating" filed in the U.S. Patent and Trademark Office on Dec. 29, 1993, now abandoned.

BACKGROUND OF THE INVENTION

The present invention relates to a mixed surfactant system.

Polymers are used extensively to make a variety of products which include blown and cast films, extruded sheets, injection molded articles, foams, blow molded articles, extruded pipe, monofilaments, and nonwoven webs. Some of such polymers, such as polyolefins, are naturally hydrophobic, and for many uses this property is either a positive attribute or at least not a disadvantage.

There are a number of uses for polymers, however, where their hydrophobic nature either limits their usefulness or requires some effort to modify the surface characteristics of the shaped articles made therefrom. By way of example, hydrophobic polymers, such as polyolefins, are used to manufacture polymeric fabrics which are employed in the construction of such disposable absorbent articles as diapers, feminine care products, incontinent products, training pants, wipes, and the like. Such polymeric fabrics often are nonwoven webs prepared by, for example, such processes as meltblowing, coforming, and spunbonding. Frequently, such polymeric fabrics need to be wettable. Wettability can be obtained by spraying or otherwise coating (i.e., surface treating or topically treating) the fabric with a surfactant solution during or after its formation, and then drying the web.

Some of the more common topically applied surfactants are nonionic surfactants, such as polyethoxylated octylphenols and condensation products of propylene oxide with propylene glycol, by way of illustration only. These surfactants are effective in rendering normally hydrophobic polymeric fabrics wettable. However, the surfactant is readily removed from the fabric, often after only a single exposure to an aqueous liquid.

Substantial efforts have been directed to increasing the durability of surfactants which are topically applied to a polymeric fabric. Such efforts include the following, by way of illustration:

(1) use of a composition which includes water, a primary surfactant, and a cosurfactant which is functional to wet the fabric with the composition and which provides for substantially uniform distribution of the primary surfactant onto the polymeric fabric;

(2) use of a surfactant, with or without a nonionic cosurfactant, which is the reaction product of an acid anhydride derivative, such as a substituted succinic anhydride, with a polyhydroxy compound, such as sorbitol, a polyethylene glycol, methanolamine, a polyhydroxyamine, certain primary, and secondary amines, and certain unsaturated aliphatic sulfo compounds;

(3) use of a surfactant, with or without a nonionic cosurfactant, which is the reaction product of certain unsaturated aliphatic sulfo compounds with the reaction product of an acid anhydride derivative, such as a substituted succinic anhydride, with a polyamine having at least one NH group capable of addition to a double bond;

(4) use of a surfactant mixture which includes an ester-acid, ester salt, or a mixture thereof and an amidic-acid amidic salt or mixture thereof with or without a nonionic cosurfactant; and (5) use of a surfactant mixture which includes a sorbitol succinate surfactant, such as an ethoxylated amino sorbitol succinate salt or an alkenyl succinate anhydride ethoxylated fatty amine salt, and a cowetting aid which can be, for example, a silicone polyether or a primary, or secondary alcohol having up to about 8 carbon atoms.

Notwithstanding the advances which have been made in rendering topically applied surfactants more durable on a polymeric fabric, i.e., more resistant to removal by an aqueous liquid, there still is a need for further improvement.

SUMMARY OF THE INVENTION

It therefore is an object of the present invention to provide a composition for increasing the resistance to removal by an aqueous liquid of surfactants from a polymeric fabric.

It also is an object of the present invention to provide a method for increasing the wettability of a polymeric fabric by the application of surfactants thereto with a concomitant increase in the resistance to removal of the surfactants from the polymeric fabric by an aqueous liquid.

It is a further object of the present invention to provide a wettable polymeric fabric to which surfactants have been applied, which surfactants are resistant to removal by an aqueous liquid.

It is another object of the present invention to provide a disposable absorbent article, at least one component of which is a wettable polymeric fabric to which surfactants have been applied, which surfactants are resistant to removal by an aqueous liquid.

These and other objects will be apparent to those having ordinary skill in the art from a consideration of the specification and claims which follow.

Accordingly, the present invention provides a composition for increasing the resistance to removal by an aqueous liquid of surfactants from a polymeric fabric composed of fibers having a plurality of fiber-fiber interstices at junctions of two or more fibers, which composition includes water, a first surfactant, and a second surfactant which is structurally dissimilar to and less soluble in water than the first surfactant, in which one of the first and second surfactants has a solubility in water at 20° C. no greater than about 5 percent by weight, based on the weight of the water.

The present invention further provides a method for increasing the wettability of a polymeric fabric by the application of surfactants thereto with a concomitant increase in the resistance to removal of the surfactants from the polymeric fabric by an aqueous liquid, which method includes providing a polymeric fabric having a surface and composed of fibers having a plurality of fiber-fiber interstices at the junctions of two or more fibers; applying to the surface of the polymeric fabric a composition, as already defined, which includes water, a first surfactant, and a second surfactant; and drying the polymeric fabric to which the composition has been applied.

The present invention additionally provides a wettable polymeric fabric to which surfactants have been applied, which surfactants are resistant to removal by an aqueous liquid, which fabric includes fibers having a plurality of fiber-fiber interstices at the junctions of two or more of the fibers, a first surfactant, and a second surfactant, in which one of the first and second surfactants has a solubility in water at 20° C. no greater than about 5 percent by weight, based on the weight of the water and the second surfactant is structurally dissimilar to and less soluble in water than the first surfactant.

In certain embodiments of the method of the present invention, the fabric is worked after the surfactant composition has been applied.

The present invention also provides a disposable absorbent article, at least one component of which is the wettable polymeric fabric as described above. Examples of disposable absorbent articles include diapers; feminine care products, such as sanitary napkins and tampons; incontinent products; training pants; and wipes.

In certain embodiments, the first and second surfactants are adapted, upon working of a polymeric fabric to which the composition has been applied, to preferentially locate in the fiber-fiber interstices and resist removal therefrom by an aqueous liquid. In other embodiments, the first surfactant has a linear structure and the second surfactant has a comb-like structure. In further embodiments, the first and second surfactants are polysiloxane polyethers. In additional embodiments, each of the first and second surfactants has a solubility in water at 20° C. no greater than about 5 percent by weight, based on the weight of the water. In still other embodiments, the first surfactant has a solubility in water at 20° C. no greater than about 5 percent by weight, based on the weight of the water, and the second surfactant is essentially insoluble in water at 20° C. In yet other embodiments, the first and second surfactants are present in a ratio by weight of the first surfactant to the second surfactant which is in a range of from about 10:1 to about 1:2. In still further embodiments, the fibers of the polymeric fabric are composed of polyolefin fibers.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE INVENTION

As used herein, the term "polymeric fabric" means a fabric prepared from any polymeric material capable of being formed into a fabric. Thus, such material can be synthetic or natural, although the former are more likely to be employed in the present invention. Examines of natural polymeric materials include, cotton, silk, wool, and cellulose, by way of illustration only.

Synthetic polymeric materials, in turn, can be either thermosetting or thermoplastic materials, with thermoplastic materials being more common. Examples of thermosetting polymers include, by way of illustration only, alkyd resins, such as phthalic anhydride-glycerol resins, maleic acid-glycerol resins, adipic acid-glycerol resins, and phthalic anhydride-pentaerythritol resins; allylic resins, in which such monomers as diallyl phthalate, diallyl isophthalate, diallyl maleate, and diallyl chlorendate serve as nonvolatile cross-linking agents in polyester compounds; amino resins, such as aniline-formaldehyde resins, ethylene urea-formaldehyde resins, dicyandiamide-formaldehyde resins, melamine-formaldehyde resins, sulfonamide-formaldehyde resins, and urea-formaldehyde resins; epoxy resins, such as cross-linked epichlorohydrin-bisphenol A resins; phenolic resins, such as phenol-formaldehyde resins, including Novolacs and resols; and thermosetting polyesters, silicones, and urethanes.

Examples of thermoplastic polymers include, by way of illustration only, end-capped polyacetals, such as poly(oxymethylene) or polyformaldehyde, poly(trichloroacetaldehyde), poly(n-valeraldehyde), poly(acetaldehyde), poly(propionaldehyde), and the like; acrylic polymers, such as polyacrylamide, poly(acrylic acid), poly(methacrylic acids, poly(ethyl acrylate), poly(methyl methacrylate), and the like; fluorocarbon polymers, such as poly(tetrafluoroethylene), perfluorinated ethylene-propylene copolymers, ethylene-tetrafluoroethylene copolymers, poly(chlorotrifluoroethylene), ethylene-chlorotrifluoroethylene copolymers, poly(vinylidene fluoride), poly(vinyl fluoride), and the like; polyamides, such as poly(6-aminocaproic acid) or poly(ε-caprolactam), poly(hexamethylene adipamide), poly(hexamethylene sebacamide), poly(11-aminoundecanoic acid), and the like; polyaramides, such as poly(imino-1,3-phenyleneiminoisophthaloyl) or poly(m-phenylene isophthalamide), and the like; parylenes, such as poly-p-xylylene, poly(chloro-p-xylylene), and the like; polyaryl ethers, such as poly)oxy-2,6-dimethyl-1,4-phenylene) or poly(p-phenylene oxide), and the like; polyaryl sulfones, such as poly(oxy-1,4-phenylenesulfonyl-1,4-phenyleneoxy-1,4-phenylene-isopropylidene-1,4-phenylene), poly(sulfonyl-1,4-phenyleneoxy-1,4-phenylenesulfonyl-4,4'-biphenylene), and the like; polycarbonates, such as poly(bisphenolA)or-poly(carbonyldioxy-1,4-phenyleneisopropylidene-1,4-phenylene), and the like; polyesters, such as poly(ethylene terephthalate), poly)tetramethylene terephthalate), poly(cyclohexylene-1,4-dimethylene terephthalate or poly(oxymethylene-1,4-cyclohexylenemethyleneoxyterephthaloyl), and the like; polyaryl sulfides, such as poly(p-phenylene sulfide) or poly(thio-1,4-phenylene), and the like; polyimides, such as poly(pyromellitimido-1,4-phenylene), and the like; polyolefins, such as polyethylene, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, polyacrylonitrile, poly(vinyl acetate), poly(vinylidene chloride), polystyrene, and the like; copolymers of the foregoing, such as acrylonitrile-butadiene-styrene (ABS) copolymers, and the like. In certain embodiments, the polymeric fabric will be prepared from a polyolefin. In other embodiments, the polyolefin will be polypropylene.

The term "fabric" is used broadly herein to mean any fibrous material which has been formed into a sheet or web. That is, the fabric is composed, at least in part, of fibers of any length. Thus, the fabric can be a woven or nonwoven sheet or web, all of which are readily prepared by methods well known to those having ordinary skill in the art. For example, nonwoven webs are prepared by such processes as meltblowing, coforming, spunbonding, and carding. Moreover, the fabric can consist of a single layer or multiple layers. When multiple layers are present, only one needs to be fibrous. Thus, a multilayered fabric can include films, scrim, and other materials which do not have the requisite fiber-fiber interstices, described below.

Regardless of whether the fabric is a woven or nonwoven fabric, the fibers of which the fabric is at least in part composed touch and/or cross in a plurality of locations. The spaces associated with these locations are referred to herein as "fiber-fiber interstices." Thus, the polymeric fabric has a plurality of fiber-fiber interstices. The spaces or interstices begin at the point where the fibers touch and extend outwardly or away from such point for a short distance along each fiber forming the interstice. Such distance is not fixed and can vary from interstice to interstice. As a practical matter, however, the distance generally can be up to perhaps ten times the diameter of the fibers involved in forming the interstices, with three or four times the diameters of the fibers being more typical.

The composition of the present invention includes water, a first surfactant, and a second surfactant which is structurally dissimilar to and less soluble in water than the first surfactant. One of the first and second surfactants will have a solubility in water at 20° C. which is no greater than about 5 percent by weight, based on the weight of the water. In certain embodiments, the first and second surfactants are present in a ratio by weight of first surfactant to second surfactant which is in a range of from about 10:1 to about 1:2. In other embodiments, the ratio of first surfactant to second surfactant is in a range of from about 5:1 to about 1:1.

In still other embodiments, the first and second surfactants are adapted, upon working of polymeric fabric to which the composition has been applied, to preferentially locate in the fiber-fiber interstices and resist removal therefrom by aqueous liquid. Simply stated, this means that the force which leads to or favors dissolution or dispersion of the surfactants in an aqueous liquid is less than the forces which favor retention of the surfactants on the surface of the fabric (i.e., on the surfaces of the fibers of which the polymeric fabric is composed) and/or in the fiber-fiber interstices of the fabric.

At least three primary forces are believed to be involved. The first is the entropy or driving force of dissolution and dispersion. Entropy, it will be remembered, is a function of the state of a system. Its value depends upon the condition of the system and not upon its past history. For an infinitesimal reversible process, the entropy change dS is given by $$dS = dq_{rev}/T \quad (1)$$

where $dq_{rev}$ is the heat absorbed from the surroundings and T is the absolute temperature. For a process that occurs spontaneously, the entropy change is greater than the heat change divided by the absolute temperature. That is, $$dS > dq_{rev}/T \quad (2)$$

For a surfactant to render the polymeric fabric wettable by an aqueous liquid, at least some of the surfactant must dissolve spontaneously in the aqueous medium in order to lower the surface tension of the aqueous medium to a value which is equal to or less than that of the fabric. Thus, it is evident that equation 2 must control. However, the durability of a surfactant on the polymeric fabric, i.e., the ability of the surfactant to resist removal by an aqueous liquid, is inversely proportional to the value of dS. Stated differently, the more soluble a surfactant is in an aqueous liquid, the greater will be the value of dS for a given value of $dq_{rev}$. It is for these reasons that one of the first and second surfactants has a solubility in water at 20° C. which is no greater than about 5 percent by weight, based on the weight of the water. In certain embodiments, each of the first and second surfactants has a solubility in water at 20° C. no greater than about 5 percent by weight, based on the weight of the water. In other embodiments, the first surfactant has a solubility in water at 20° C. no greater than about 5 percent by weight, based on the weight of the water, and the second surfactant is essentially insoluble in water.

The second force is the force of adhesion or attraction of the surfactants on the fibers. This force is a function of the molecular attractions between the surfactants and the polymer of which the fabric is composed, e.g., dipole-dipole and van der Waals forces. The second force alone can counter the first force and, if sufficiently strong, can result in a relatively durable coating.

The third is a capillary, force which results from the formation of fiber-fiber interstices; it is a function of the surface tension of each surfactant and is in part responsible for the preferential movement of surfactant to the fiber-fiber interstices. The second and third forces work together to keep the surfactants in the fiber-fiber interstices, in opposition to the first force. The balancing of these three forces is what is meant by the phrase, "preferentially locate in the fiber-fiber interstices and resist removal therefrom by aqueous liquid." That is, the first and second surfactants are selected in some embodiments to provide strong second and third forces, in comparison to the first force. One factor in so doing, as noted above, is to select surfactants having limited solubilities in water.

As already stated, the first and second surfactants are structurally dissimilar. The term "structurally dissimilar" refers primarily to the configuration of a surfactant, that is, the particular arrangement of atoms or groups in space that is characteristic of the surfactant, and secondarily to the types or compositions of one or moieties or groups which may be present. In general, if the two surfactants have different configurations, the types or compositions of the moieties of which the surfactant is composed need not be considered. The more common configurations are linear and comb-like, i.e., a substantially linear backbone with at least two substituents which extend outwardly or away from the backbone. If both surfactants have the same configuration, e.g., both are linear, then one surfactant should have at least one moiety or group which is not found in the other surfactant.

By way of illustration of the foregoing principles, a polyethoxylated n-octylphenol is not structurally dissimilar to a polyethoxylated isooctylphenol, but is structurally dissimilar to the condensation product of propylene oxide with propylene glycol. Similarly, an A-B-A polysiloxane polyether is structurally dissimilar to an $(A-B)_n$ polysiloxane polyether, even if the A and B moieties are essentially the same.

In certain embodiments, one of the first and second surfactants will have a linear structure. An example of a class of surfactants having a linear structure is what are commonly referred to as A-B-A polymers, in which A represents the moiety which imparts surfactant properties to the molecule and B represents the remainder of the molecule and of ten includes repeating units. Those having ordinary, skill in the art will recognize that in many instances B can be represented as B'-C, in which C represents a group which links B' with A, and B' represents that portion of B which consists of repeating units. In other embodiments, one of the first and second surfactants is a polysiloxane polyether. In still other embodiments, each of the first and second surfactants is a polysiloxne polyether.

In certain embodiments, one of the first and second surfactants is an A-B-A polysiloxane polyether surfactant having general formula I.

$$R_1O(C_3H_6O)_a(C_2H_4O)_b(CH_2)_c-\underset{\underset{R_3}{|}}{\overset{\overset{R_2}{|}}{Si}}-O\underset{d}{)_{\overline{d}}}\underset{\underset{R_5}{|}}{\overset{\overset{R_4}{|}}{Si}}-(CH_2)_cO(C_2H_4O)_b(C_3H_6O)_aR_6$$

wherein:

each of $R_1$ and $R_6$ independently is selected from the group consisting of hydrogen and $C_1-C_8$ alkyl and aryl groups;

each of $R_2-R_4$ independently is selected from the group consisting of $C_1-C_8$ alkyl and aryl groups;

a represents an integer from about 8 to about 25;

b represents an integer from about 8 to about 25;

the ratio of b to a is in a range of from about 0.7 to about 1.5;

c represents an integer from 1 to about 10;

d represents an integer from about 40 to about 100;

the ratio of d to two times the sum of a and b is in a range of from about 0.7 to about 1.5; and the number-average molecular weight of said first surfactant is in a range of from about 5,000 to about 35,000. In other embodiments, each of $R_1$ and $R_6$ independently is selected from the group consisting of hydrogen and $C_1-C_3$ alkyl and phenyl groups;

each of $R_2-R_4$ independently is selected from the group consisting of $C_1-C_3$ alkyl and phenyl groups;

a represents an integer from about 12 to about 18;

b represents an integer from about 12 to about 18;

the ratio of b to a is about 1;

c represents an integer from about 2 to about 4;

d represents an integer from about 50 to about 70;

the ratio of d to two times the sum of a and b is about 1; and the number-average molecular weight of said first surfactant is in a range of from about 6,500 to about 18,500. In yet other embodiments, each of $R_1$ and $R_6$ is hydrogen;

each of $R_2-R_4$ is a methyl group;

a represents an integer which is about 15;

b represents an integer which is about 15;

c represents an integer which is 3;

d represents an integer which is about 60; and the number-average molecular weight of the first surfactant is about 7,000.

In certain other embodiments, one of the first and second surfactants will have a comb-like structure. An example of a class of surfactants which has a comb-like structure is what are commonly referred to as (A-B)$_n$ polymers, in which A represents the moiety which imparts surfactant properties to the molecule and B represents the remainder of the molecule.

In certain embodiments, one of the first and second surfactants is an (A-B)$_n$ polysiloxane polyether surfactant having general formula II.

$$R_7-\underset{\underset{R_9}{|}}{\overset{\overset{R_8}{|}}{Si}}-O-(\underset{\underset{R_{11}}{|}}{\overset{\overset{R_{10}}{|}}{Si}}-O)_{\overline{e}}(\underset{\underset{R_{17}}{|}}{\overset{\overset{R_{12}}{|}}{Si}}-O)_{\overline{f}}(\underset{\underset{CH_2}{|}}{\overset{\overset{R_{13}}{|}}{Si}}-O)_{\overline{g}}\underset{\underset{R_{16}}{|}}{\overset{\overset{R_{14}}{|}}{Si}}-R_{15}$$
$$(CH_2)_hO(C_2H_4O)_j(C_3H_6O)_kR_{18}$$

wherein:

each of $R_7-R_{16}$ independently is selected from the group consisting of $C_1-C_8$ alkyl and aryl groups;

$R_{17}$ is a $C_{10}-C_{25}$ alkyl group;

$R_{18}$ is hydrogen or a $C_1-C_4$ alkyl group;

e represents an integer from about 3 to about 15;

f represents an integer from about 1 to about 6;

g represents an integer from about 5 to about 30;

the ratio of f to g is in a range of from about 2 to about 10;

h represents an integer from 1 to about 10;

j represents an integer from about 4 to about 15;

k represents an integer from about 1 to about 15;

the ratio of j to k is in a range of from about 0.5 to about 4; and the number-average molecular weight of the second surfactant is in a range of from about 5,000 to about 60,000.

In other embodiments, each of $R_7-R_{16}$ independently is selected from the group consisting of $C_1-C_3$ alkyl and phenyl groups;

$R_{17}$ is a $C_{12}-C_{20}$ alkyl group;

$R_{18}$ is hydrogen or a $C_1-C_3$ alkyl group;

e represents an integer from about 3 to about 8;

f represents an integer from about 2 to about 4;

g represents an integer from about 10 to about 20;

the ratio of f to g is in a range of from about 3 to about 8;

h represents an integer from about 2 to about 4;

j represents an integer from about 6 to about 12;

k represents an integer from about 4 to about 8;

the ratio of j to k is in a range of from about 1 to about 2; and the number-average molecular weight of the second surfactant is in a range of from about 7,000 to about 24,000.

In yet other embodiments, each of $R_7-R_{16}$ is a methyl group;

$R_{17}$ is a hexadecyl group;

$R_{18}$ is hydrogen;

e represents an integer which is about 5;

f represents an integer which is about 3;

g represents an integer which is about 15;

h represents an integer which is 2;

j represents an integer which is about 9;

k represents an integer which is about 6; and the number-average molecular weight of the second surfactant is about 14,500.

In certain additional embodiments, the first surfactant is an A-B-A polysiloxane polyether having general formula I and the second surfactant is an $(A-B)_n$ polysiloxane polyether having general formula II.

While the description of the composition makes particular reference to a first surfactant and a second surfactant, such reference does not preclude the presence of more than two surfactant types, either in the composition or on the fibers of a polymeric fabric. In addition, either or both of the first surfactant and the second surfactant can include two or more surfactants. Moreover, the designation of the required two surfactants as first surfactant and second surfactant is for convenience only, and is not to be construed as limiting in any way the scope of the present invention.

The levels of the first and second surfactants in the composition can vary over a wide range. In general, the level of the surfactants in the composition is a function of the amount of the surfactants which is desired to be added to the polymeric fabric. As a practical matter, the level of the surfactants in the composition typically will be in a range of from about 0.01 to about 3 percent by weight, based on the weight of water. Depending on the level of add-on desired, however, lower or higher levels can be employed. In certain embodiments, the level of surfactants in the composition will be in a range of from about 0.01 to about 1 percent by weight.

The composition of the present invention described above is useful for increasing the wettability of a polymeric fabric by the application of surfactants thereto, with a concomitant increase in the resistance to removal of surfactant from the polymeric fabric by an aqueous liquid. The method for accomplishing such increases involves providing a polymeric fabric having a surface and composed of fibers having a plurality of fiber-fiber interstices at the junctions of two or more fibers, applying to the surface of the polymeric fabric a composition of the present invention as already described, and drying the polymeric fabric to which the composition has been applied.

In the first step of the method of the present invention, a polymeric fabric is provided, which fabric has a surface and is composed of fibers having a plurality of fiber-fiber interstices at the junctions of two or more fibers. The polymeric fabric and its characteristics were described in detail earlier.

The next step involves applying to the surface of the polymeric fabric a composition of the present invention as already described. In general, application of the composition can be by any means known to those having ordinary, skill in the art. Such means include, by way of illustration only, dipping, doctor blading, spraying, and direct and offset gravure printing or coating.

Drying of the treated polymeric fabric can be accomplished by any known means. Examples of known drying means include, by way of illustration only, convection ovens, radiant heat, infrared radiation, forced air ovens, and heated rolls or cans. Drying also includes air drying without the addition of heat energy, other than that present in the ambient environment. The polymeric fabric which is obtained after the drying step is wettable. Moreover, the surfactants are resistant to removal by an aqueous liquid.

If desired, an additional step can be employed in order to increase the resistance of the surfactants to removal by an aqueous liquid. Such step involves working the polymeric fabric to which the composition has been applied to an extent sufficient to preferentially locate a substantial portion of the first and second surfactants in fiber-fiber interstices of the polymeric fabric. As used herein, the term "working" means subjecting the polymeric fabric to compressive forces after the surfactant composition has been applied thereto. Working can be carried out before, during, or after the drying step by any means which will subject the polymeric fabric to compressive forces. For example, the polymeric fabric can be passed through nip rolls, such as press or calendaring rolls. Alternatively, the polymeric fabric can be compressively sandwiched between a rotating drum or roll and an outer belt or web; the rotating drum or roll can be heated, if desired. Other methods will be apparent to those having ordinary skill in the art.

The most effective means known for working the fabric involves simply subjecting the treated fabric to a compression step after the composition has been applied to a surface. The application of the composition to the surface and the subsequent working of the treated fabric are readily combined into a sequential operation, such as that involved in a dip-and-nip procedure. A dip-and-nip procedure has the added advantage of removing excess composition which reduces the energy and time required for the final drying step. When a working step is included, the surfactants preferentially are located in the fiber-fiber interstices at the junctions of two or more fibers.

The amount of surfactants present on the polymeric fabric in general will be at least about 0.3 percent by weight, based on the weight of the polymeric fabric. As a practical matter, the amount of surfactant present typically will be in a range of from about 0.3 to about 5 percent by weight. In certain embodiments, the amount of surfactant present on the fabric will be in a range of from about 0.5 to about 3 percent by weight. In other embodiments, the amount of surfactant present on the fabric will be in a range of from about 0.7 to about 2 percent by weight.

The wettable polymeric fabric of the present invention is well-suited as a component of a disposable absorbent article. Examples of disposable absorbent articles include, by way of illustration only, diapers; feminine care products, such a sanitary, napkins and tampons; incontinent products; training pants; and wipes.

The present invention is further described by the examples which follow. Such examples, however, are not to be construed as limiting in any way either the spirit or the scope of the present invention. In the examples, all parts are by weight, unless stated otherwise.

EXAMPLE 1

The polymeric fabric employed was a spunbonded polypropylene nonwoven web having a basis weight of about 1.6 ounces per square yard or osy (about 38 grams per square meter or $g/m^2$). A sample of the fabric 5×15 inches (about 13×38 cm) was weighed and placed in a 1-liter beaker containing 500 ml of a 0.1 percent by weight solution of surfactants in water. After 20 seconds, the sample was removed from the beaker and passed through an Atlas Laboratory Wringer with a 25-lb (1 1,4-kg) nip setting (Atlas Electric Devices Company, Chicago. Ill.). The sample was dried in a convection oven (Pro-Tronix® II, General Signal Company, Blue Island, Ill.) at about 85° C. for about 20 minutes. The dried sample then was weighed and the add-on of surfactants calculated.

Three surfactants were employed. The first, Surfactant A, was a linear polysiloxane polyether having the formula, The number-average molecular weight of the surfactant was about 7,000. It had a mean viscosity at 25° C. of 1,850 centistokes and a mean specific gravity at the same temperature of 1.01 g/cm³.

The second, Surfactant B, was a polyethoxylated octylphenol surfactant, Triton® X-102 (Rohm and Haas Co., Philadelphia, Pa.).

The third surfactant, Surfactant C, was a comb-like polysiloxane polyether having the formula.

The number-average molecular weight of the surfactant was about 14,500. The material had a mean viscosity at 25° C. of 900 centistokes and a mean specific gravity at 20° C. of 0.93 g/cm³. The mean refractive index of the material at 20° C. was 1.438.

Those having ordinary skill in the art will recognize that Surfactant A is of the type of polysiloxane polyether represented by general formula I. Similarly, Surfactant C is of the type of polysiloxane polyether represented by general formula II. Significantly, neither of these surfactants is considered to be a surfactant for aqueous systems. This is especially true of Surfactant C.

Several different combinations and ratios of surfactants were studied. The first combination consisted of a 3:1 ratio by weight of Surfactant A to Surfactant C (Sample A). The second combination consisted of a 1:1 ratio by weight of the same surfactants employed for Sample A (Sample B). The third combination consisted of a 1:1 ratio by weight of Surfactant B to Surfactant A (Sample C). In addition, two controls were included and consisted of Surfactant A alone (Sample D) and Surfactant B alone (Sample E).

Each fabric sample to which one or more surfactants had been added was washed by placing the sample in a 1-liter conical flask containing 500 ml of tap water at ambient temperature. The flask was stoppered, placed on a wrist-action shaker (Burrell Scientific, Pittsburgh, Pa.), and gently shaken for one minute. The sample was removed from the flask, carefully squeezed by hand, and passed through a laboratory wringer having a nip setting of 25 lb (11.4 kg). The sample then was dried and weighed as described above. The percent surfactant lost was calculated as follows:

Percent lost=100×[(g TPF—g. PF)−(g WTPF—g. PF)/(g TPF—g. PF)]

wherein "g TPF" refers to the dry weight of the treated polymeric fabric, "g PF" refers to the dry weight of the original fabric sample before treatment, and "g WTPF" refers to the dry weight of treated polymeric fabric which has been washed. The washing procedure was repeated until a sample no longer was wettable with water. As can be seen from the above equation, all percent surfactant lost calculations are cumulative.

The wettability of each sample was estimated by placing drops of water on the sample and measuring the time required for complete penetration of the water drops into the fabric referred to hereinafter as "wetting time" or "WT"). Each sample was tested with a minimum of five drops of water placed in five different locations. The time for all of the drops to penetrate into the sample was measured. The rsults are summarized in Table 1. In the table, "WT" represents the wetting time in seconds and "Lost" represents the cumulative percent surfactant lost after the stated number of washings. The initial add-on values in percent by weight also are given for each sample.

TABLE 1

Summary of Washing Results for Worked Samples

| % Add-on Status | Sample A 1.0 | | Sample B 0.9 | | Sample C 1.2 | | Sample D 1.1 | | Sample E 1.0 | |
|---|---|---|---|---|---|---|---|---|---|---|
| | WT | Lost | WT | Lost | WT | Lost | WT | Lost | WT | Lost |
| 1st Wash | <1 | 4 | <1 | 11 | <1 | 47 | <1 | 18 | <1 | 83 |
| 2nd Wash | <1 | 9 | <1 | 20 | <1 | 59 | <1 | 32 | NW[a] | 97 |
| 3rd Wash | <1 | 16 | <1 | 29 | <1 | 64 | <1 | 54 | — | — |
| 4th Wash | <1 | 21 | <1 | 35 | <1 | 72 | <1 | 62 | — | — |
| 5th Wash | <1 | 29 | <1 | 42 | NW | 88 | <1 | 62 | — | — |
| 6th Wash | <1 | 34 | <1 | 49 | — | — | <1 | 76 | — | — |
| 7th Wash | <1 | 44 | <1 | 57 | — | — | <1 | 84 | — | — |
| 8th Wash | <1 | 52 | <1 | 66 | — | — | NW | 96 | — | — |
| 9th Wash | <1 | 61 | <1 | 73 | — | — | — | — | — | — |
| 10th Wash | <1 | 67 | PW[b] | 84 | — | — | — | — | — | — |
| 11th Wash | <1 | 72 | NW | — | — | — | — | — | — | — |
| 12th Wash | <1 | 76 | — | — | — | — | — | — | — | — |
| 13th Wash | <1 | 80 | — | — | — | — | — | — | — | — |
| 14th Wash | PW | 86 | — | — | — | — | — | — | — | — |

[a]NW means nonwettable.
[b]PW means that wetting was patchy, i.e., some of the drops did not wet the fabric.

From Table 1, it is clear that the mixed surfactants of Samples A, B, and C gave superior results. That is, the results for Sample C were superior to the results for Sample E, and the results for Samples A and B were superior to the results for Sample D.

Figure 1:
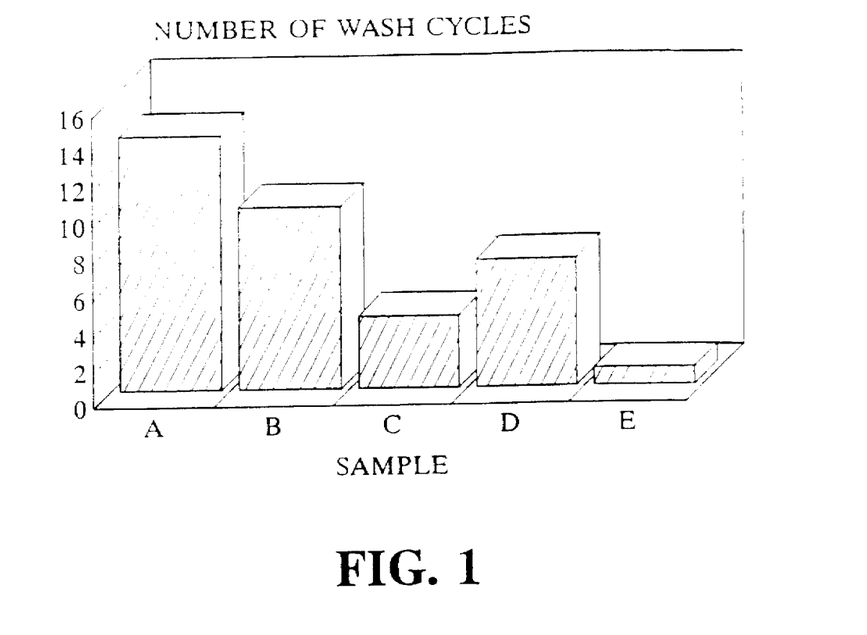
FIGS. 1 and 2 are three-dimensional plots of the maximum number of wash cycles achieved without losing wettability versus percent surfactant lost for five polymeric fabric samples having different surfactant compositions applied to the fabric with and without working, respectively.

To better understand the data in Table 1, such results were plotted three dimensionally in FIG. 1 as the maximum number of wash cycles achieved without completely losing wettability versus percent surfactant lost for all five polymeric fabric samples. The figure clearly shows the improved resistance to removal of a mixed surfactant system of the present invention, when compared to a single surfactant. FIG. 1 also shows the advantages to be obtained when both the first surfactant and the second surfactant are polysiloxane polyether surfactants.

EXAMPLE 2

In order to demonstrate the need for the fabric to be worked after the composition of the present invention has been applied, the procedure of Example 1 was repeated, except that in each case the composition was applied to the fabric by spraying and the size of each sample was 5×5 inches (about 13×13 cm). Each sample was hung in a fume hood and sprayed by means of a 16-ounce (roughly 0.5-liter) Preval Power Unit (Precision Valve Corporation, Yonkers, N.Y.) on both sides of the fabric with a 0.1 percent by weight solution of surfactants in water. The sprayed fabric then was dried, weighed, and washed as described in Example 1. Since the same surfactant compositions were employed in this example as in Example 1, the sample designations are followed by the letter "S" to indicate sprayed samples.

Figure 2:
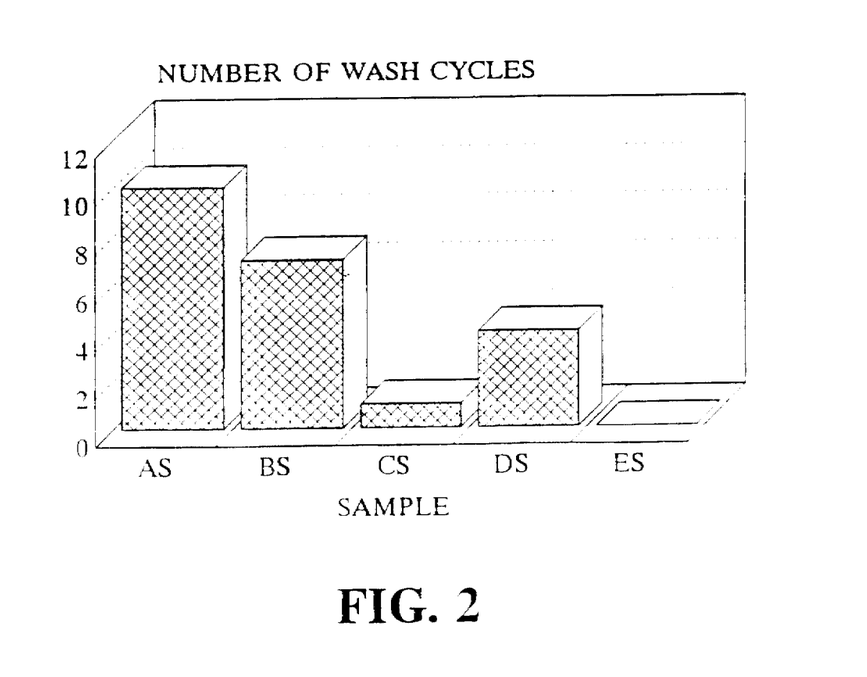
Figure 3:
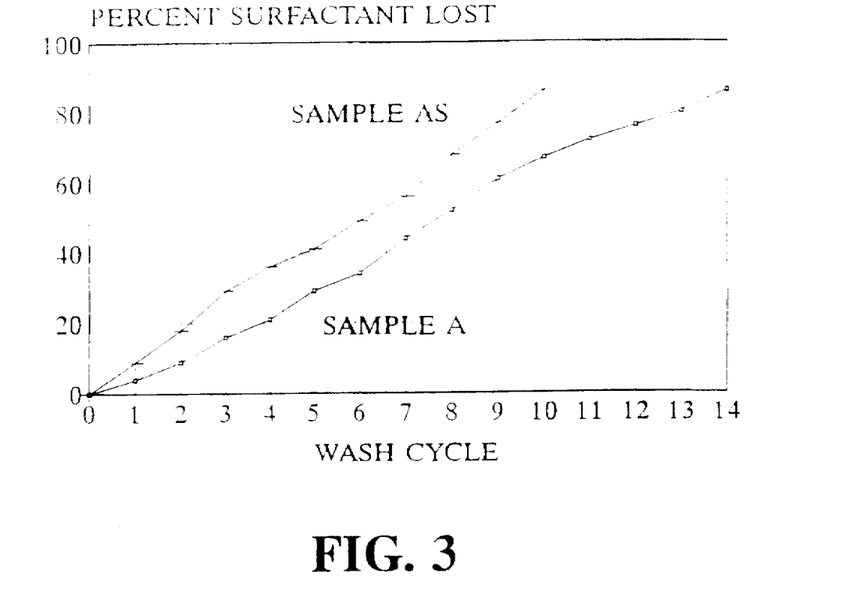
FIGS. 3–5 are plots of wash cycle versus percent surfactant lost for three different surfactant compositions applied to the fabric with and without a subsequent working step.
Figure 4:
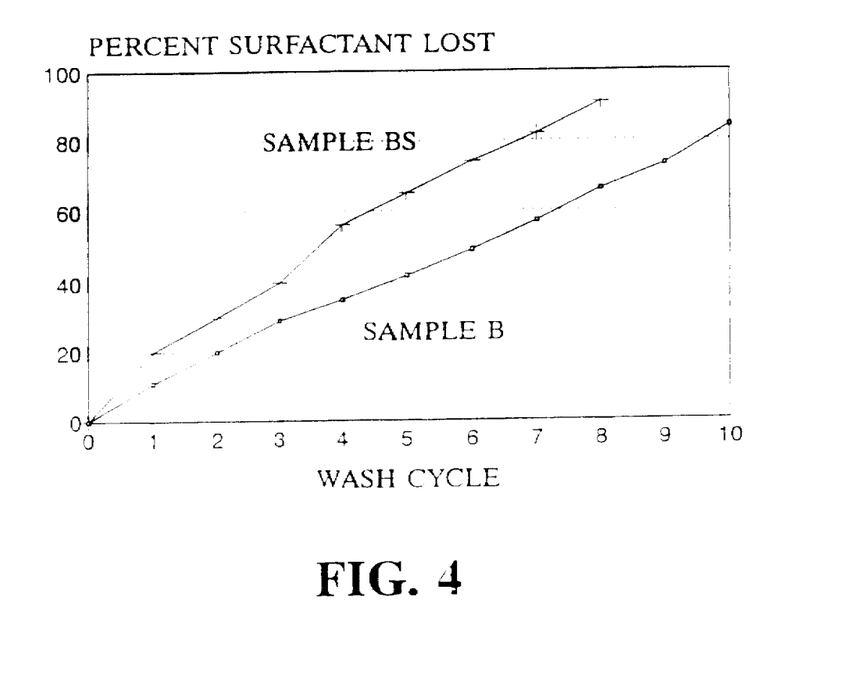
Figure 5:
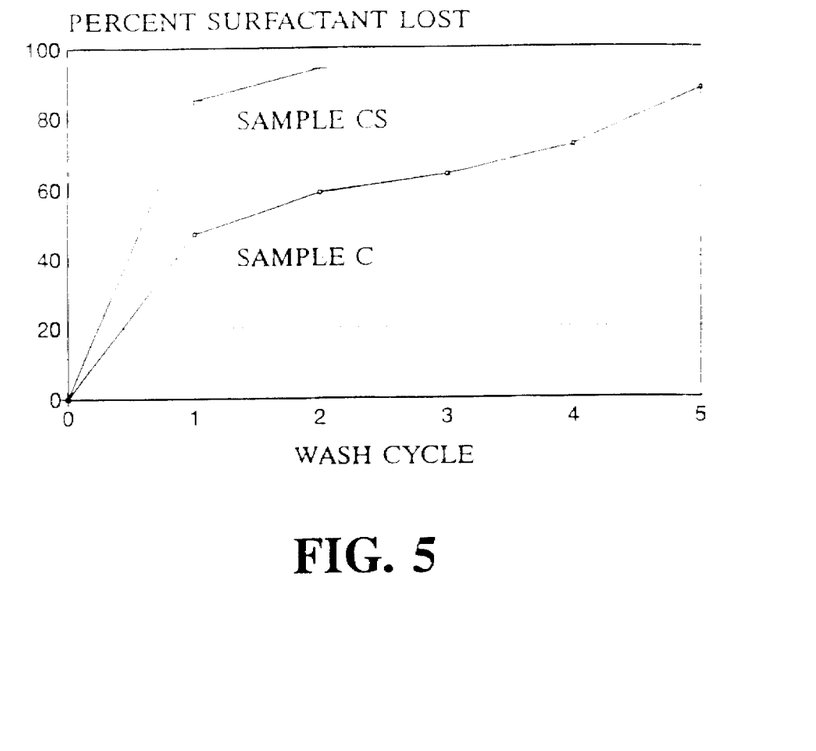

In addition to FIG. 2, the data for Samples A and AS from Tables 1 and 2 were plotted as wash cycle versus percent surfactant lost, as shown in FIG. 3. Similar plots were prepared for Samples B and BS and for Samples C and CS, as shown in FIGS. 4 and 5, respectively.

Figure 6:
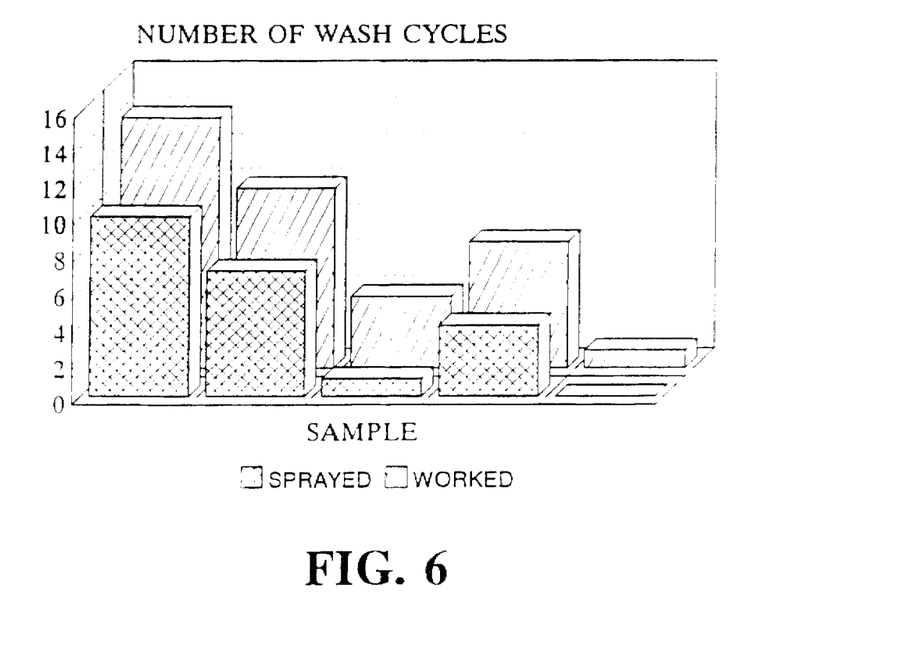
FIG. 6 is a three dimensional plot which combines the data of FIGS. 1 and 2.

Finally, the data in FIGS. 1 and 2 were combined in the three-dimensional plot shown in FIG. 6 to emphasize the advantages obtained from working the fabric after a surfactant composition has been applied to a surface.

Figure 7:
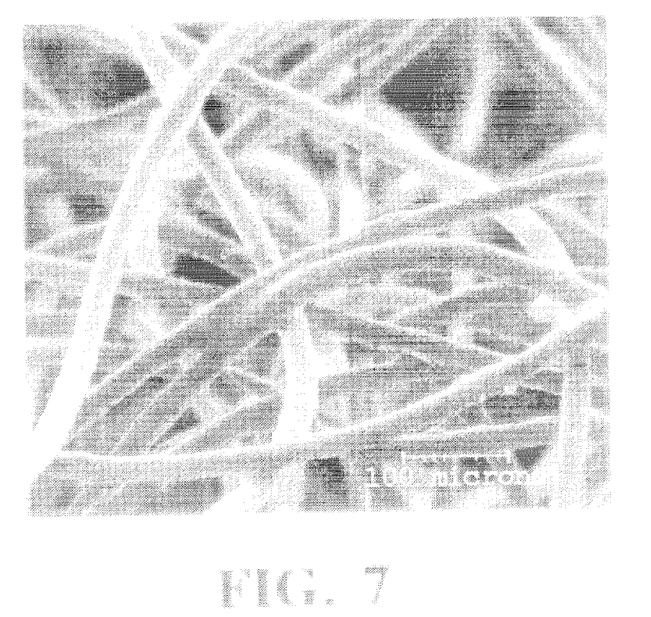
FIG. 7 is a scanning electron photomicrograph of wettable polymeric fabric prepared in accordance with one embodiment of the present invention.

In order to determine the location of the surfactants on the fabric after it has been worked and dried, dot element maps were prepared in accordance with known procedures. A scanning electron photomicrograph was obtained for a portion of the fabric of Sample A and is shown in FIG. 7. A set of element maps then was obtained, in which each showed an image that appeared at the same 128 pixel resolution as the x-ray data. Thus, there is an exact correspondence between the electron and x-ray images.

Figure 8:
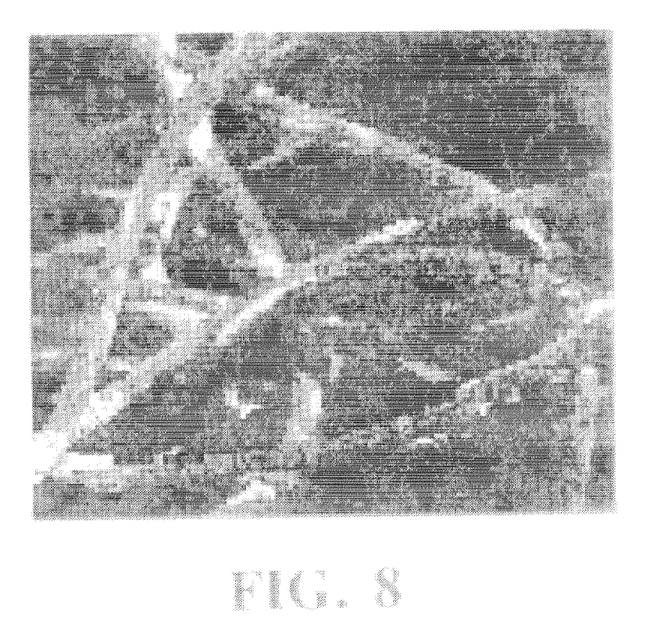
FIG. 8 is a silicon map demonstrating the preferential location of surfactants in the fiber-fiber interstices of the polymeric fabric of FIG. 7.

The purpose of the maps is to graphically illustrate variations in the local concentrations of any given element. There are, however, several factors which affect the measured x-ray intensity. Most notable are the high x-ray background associated with silicon and the surface roughness of the fabric which creates shadows in the element maps. These image artifacts were compensated for by mapping for an element that is not present in the sample, such as argon or aluminum, which has an x-ray background similar to that of the element in question, i.e., silicon. The background map then was subtracted from the silicon map to produce a true rendition of the silicon distribution. The image was further enhanced by using a "thermal" pseudo-

TABLE 2

Summary of Washing Results for Sprayed Samples

| % Add-on | Sample AS 1.0 | | Sample BS 0.9 | | Sample CS 1.1 | | Sample DS 1.0 | | Sample ES 1.1 | |
|---|---|---|---|---|---|---|---|---|---|---|
| Status | WT | Lost | WT | Lost | WT | Lost | WT | Lost | WT | Lost |
| 1st Wash | <1 | 9 | <1 | 20 | <1 | 85 | <1 | 28 | NW$^a$ | 96 |
| 2nd Wash | <1 | 18 | <1 | 30 | NW | 94 | <1 | 50 | — | — |
| 3rd Wash | <1 | 29 | <1 | 40 | — | — | <1 | 70 | — | — |
| 4th Wash | <1 | 36 | <1 | 56 | — | — | PW$^b$ | 87 | — | — |
| 5th Wash | <1 | 41 | <1 | 65 | — | — | NW | 96 | — | — |
| 6th Wash | <1 | 49 | <1 | 74 | — | — | — | — | — | — |
| 7th Wash | <1 | 56 | PW | 82 | — | — | — | — | — | — |
| 8th Wash | <1 | 68 | NW | 91 | — | — | — | — | — | — |
| 9th Wash | <1 | 77 | — | — | — | — | — | — | — | — |
| 10th Wash | PW | 86 | — | — | — | — | — | — | — | — |
| 11th Wash | NW | — | — | — | — | — | — | — | — | — |

$^a$NW means nonwettable.
$^b$PW means that wetting was patchy or spotty, i.e., some of the drops did not wet the fabric.

Upon comparing the data in Table 2 with that in Table 1, it is seen that working results in significant increases in the durability of the surfactant treatment, i.e., the resistance to removal of the surfactants from the fabric by an aqueous liquid. As with Example 1, the results were plotted three dimensionally as the maximum number of wash cycles achieved without completely losing wettability versus percent surfactant lost for all five polymeric fabric samples. Such plot is shown as FIG. 2. Even without working, a mixed surfactant system of the present invention has increased resistance to removal from the fabric by an aqueous liquid.

color look up table (LUT) and is shown in FIG. 8. This highly intuitive color scale shows areas of high silicon concentration as yellow, areas of little or no silicon as black or blue, and intermediate silicon levels as magenta. Because the maps were 30-minute maps, there was a significant level of statistical noise. The statistical variability can be reduced by acquiring the maps over a longer period of time.

It is clear from FIGS. 7 and 8 that the silicon-containing surfactants were distributed preferentially in regions of high capillary tension, i.e., in the fiber-fiber interstices of the fabric. In addition, some surfactant was distributed along the surfaces of the fibers, but not uniformly and not at the high levels found in the interstices.

Having thus described the invention, numerous changes and modifications thereof will be readily apparent to those having ordinary skill in the art without departing from the spirit or scope of the invention.

What is claimed is:

1. A wettable polymeric fabric to which surfactants have been applied, which surfactants are resistant to removal by an aqueous liquid, which fabric comprises:

fibers having a plurality of fiber-fiber interstices at the junctions of two or more of said fibers;

a first surfactant; and a second surfactant;

in which:

one of said first and second surfactants has a solubility in water at 20° C. no greater than about 5 percent by weight, based on the weight of the water;

said second surfactant is structurally dissimilar to and less soluble in water than said first surfactant; and said first and second surfactants preferentially are located in the fiber-fiber interstices.

2. The wettable polymeric fabric of claim 1, in which one of said first and second surfactants has a linear structure and the other of said first and second surfactants has a comb-like structure.

3. The wettable polymeric fabric of claim 1, in which each of said first and second surfactants has a solubility in water at 20° C. no greater than about 5 percent by weight, based on the weight of the water.

4. The wettable polymeric fabric of claim 3, in which said second surfactant is essentially insoluble in water at 20° C.

5. The wettable polymeric fabric of claim 1, in which said fibers are comprised of polyolefin fibers.

6. The wettable polymeric fabric of claim 1, in which one of said first and second surfactants has the general formula, wherein:

each of $R_1$ and $R_6$ independently is selected from the group consisting of hydrogen and $C_1$–$C_8$ alkyl and aryl groups;

each of $R_2$–$R_4$ independently is selected from the group consisting of $C_1$–$C_8$ alkyl and aryl groups;

a represents an integer from about 8 to about 25;

b represents an integer from about 8 to about 25;

the ratio of b to a is in a range of from about 0.7 to about 1.5;

c represents an integer from 1 to about 10;

d represents an integer from about 40 to about 100;

the ratio of d to two times the sum of a and b is in a range of from about 0.7 to about 1.5; and the number-average molecular weight of said first surfactant is in a range of from about 5,000 to about 35,000.

7. The wettable polymeric fabric of claim 1, in which one of said first and second surfactants has the general formula, wherein:

each of $R_7$–$R_{16}$ independently is selected from the group consisting of $C_1$–$C_8$ alkyl and aryl groups;

$R_{17}$ is a $C_{10}$–$C_{25}$ alkyl group;

$R_{18}$ is hydrogen or a $C_1$–$C_4$ alkyl group;

e represents an integer from about 3 to about 15;

f represents an integer from about 1 to about 6;

g represents an integer from about 5 to about 30;

the ratio of f to g is in a range of from about 2 to about 10;

h represents an integer from 1 to about 10;

j represents an integer from about 4 to about 15;

k represents an integer from about 1 to about 15;

the ratio of j to k is in a range of from about 0.5 to about 4; and the number-average molecular weight of the second surfactant is in a range of from about 5,000 to about 60,000.

8. The wettable polymeric fabric of claim 1, in which:

said first surfactant has the general formula, wherein:

each of $R_1$ and $R_6$ independently is selected from the group consisting of hydrogen and $C_1$–$C_8$ alkyl and aryl groups;

each of $R_2$–$R_4$ independently is selected from the group consisting of $C_1$–$C_8$ alkyl and aryl groups;

a represents an integer from about 8 to about 25;

b represents an integer from about 8 to about 25;

the ratio of b to a is in a range of from about 0.7 to about 1.5;

c represents an integer from 1 to about 10;

d represents an integer from about 40 to about 100;

the ratio of d to two times the sum of a and b is in a range of from about 0.7 to about 1.5; and the number-average molecular weight of said first surfactant is in a range of from about 5,000 to about 35,000; and said second surfactant has the general formula, wherein:

each of $R_7$–$R_{16}$ independently is selected from the group consisting of $C_1$–$C_8$ alkyl and aryl groups;

$R_{17}$ is a $C_{10}$–$C_{25}$ alkyl group;

$R_{18}$ is hydrogen or a $C_1$–$C_4$ alkyl group;

e represents an integer from about 3 to about 15;

f represents an integer from about 1 to about 6;

g represents an integer from about 5 to about 30;

the ratio of f to g is in a range of from about 2 to about 10;

h represents an integer from 1 to about 10;

j represents an integer from about 4 to about 15;

k represents an integer from about 1 to about 15;

the ratio of j to k is in a range of from about 0.5 to about 4; and the number-average molecular weight of the second surfactant is in a range of from about 5,000 to about 60,000.

9. The wettable polymeric fabric of claim 8, in which:

each of $R_1$ and $R_6$ independently is selected from the group consisting of hydrogen and $C_1$–$C_3$ alkyl and phenyl groups; each of $R_2$–$R_4$ independently is selected from the group consisting of $C_1$–$C_3$ alkyl and phenyl groups;

a represents an integer from about 12 to about 18;

b represents an integer from about 12 to about 18;

the ratio of b to a is about 1;

c represents an integer from about 2 to about 4;

d represents an integer from about 50 to about 70;

the ratio of d to two times the sum of a and b is about 1; and the number-average molecular weight of said first surfactant is in a range of from about 6,500 to about 18,500.

10. The wettable polymeric fabric of claim 8, in which:

each of $R_7$–$R_{16}$ independently is selected from the group consisting of $C_1$–$C_3$ alkyl and phenyl groups;

$R_{17}$ is a $C_{12}$–$C_{20}$ alkyl group;

$R_{18}$ is hydrogen or a $C_1$–$C_3$ alkyl group;

e represents an integer from about 3 to about 8;

f represents an integer from about 2 to about 4;

g represents an integer from about 10 to about 20;

the ratio of f to g is in a range of from about 3 to about 8;

h represents an integer from about 2 to about 4;

j represents an integer from about 6 to about 12;

k represents an integer from about 4 to about 8;

the ratio of j to k is in a range of from about 1 to about 2; and the number-average molecular weight of the second surfactant is in a range of from about 7,000 to about 24,000.

11. The wettable polymeric fabric of claim 8, in which the ratio of said first surfactant to said second surfactant is in a range of from about 10:1 to about 1:2.

12. The wettable polymeric fabric of claim 11, in which the ratio of said first surfactant to said second surfactant is in a range of from about 5:1 to about 1:1.

13. A disposable absorbent article, at least one component of which is the wettable polymeric fabric of claim 1.

14. A disposable absorbent article, at least one component of which is the wettable polymeric fabric of claim 8.

15. The disposable absorbent article of claim 14, in which said disposable absorbent article is a diaper.

16. The disposable absorbent article of claim 14, in which said disposable absorbent article is a feminine care product.

17. The disposable absorbent article of claim 16, in which said disposable absorbent article is a sanitary napkin.

18. The disposable absorbent article of claim 16, in which said disposable absorbent article is a tampon.

19. The disposable absorbent article of claim 14, in which said disposable absorbent article is an incontinent product.

20. The disposable absorbent article of claim 14, in which said disposable absorbent article is a training pant.

21. The disposable absorbent article of claim 14, in which said disposable absorbent article is a wipe.

* * * * *

UNITED STATES PATENT AND TRADEMARK OFFICE

CERTIFICATION OF CORRECTION

PATENT NO. : 5,618,614

DATED : April 8, 1997

INVENTOR(S): Ronald S. Nohr et al.

It is certified that error appears in the above-identified patent and that said Letters Patent is hereby corrected as shown below:

Column 1, line 59, "methanolamine" should read --triethanolamine--; line 60, "primary," should read --primary--;

Column 2, line 2, "thereof" (first occurrence) should read --thereof,--, "amidic-acid" should read --amidic-acid,--; line 3, "thereof" (second occurrence) should read --thereof,--; line 9, "primary," should read --primary--; line 13, "fabric. i.e. ." should read --fabric. i.e.,--;

Column 3, line 44, "live" should read --five--; line 67, "Examines" should read --Examples--;

Column 4, line 2, "only," should read --only.--; line 14, "resins." should read --resins,--; line 27, "acids," should read --acid)--; line 40, "poly)" should read --poly(--; line 57, "butadiene." should read --butadiene,--;

Column 6, line 24, "capillary," should read --capillary--;

Column 7, line 1, "of ten" should read --often-- and "ordinary," should read --ordinary--; line 34, "5.000 to about 35.000" should read --5,000 to about 35,000--; line 60, "7.000" should read --7,000--;

Column 8, lines 36 and 56, "embodiments." should read --embodiments,--;

Column 9, line 49, "ordinary," should read --ordinary--;

Column 10, line 41, sanitary," should read --sanitary--; line 60, "(11,4-kg)" should read --(11.4-kg)--; line 61, "Chicago." should read --Chicago,--;

Column 11, line 9, "7.000" should read --7,000--; line 12, "polyethoxytated" should read --polyethoxylated--;

UNITED STATES PATENT AND TRADEMARK OFFICE
CERTIFICATE OF CORRECTION

Page 2 of 2

PATENT NO. : 5,618,614
DATED : April 8, 1997
INVENTOR(S) : Ronald S. Nohr, et. al.

It is certified that error appears in the above-indentified patent and that said Letters Patent is hereby corrected as shown below:

Column 12, line 14, "scientific." should read --scientific,--; line 21, "[(gTPF-g,PF)-(gWTPF-g,PF)/(gTPF-g," should read --[(gTPF-gPF)-(gWTPF-gPF)/(gTPF-g--; line 23, "dry," should read --dry--; line 34, "referred" should read --(referred--; line 38, "In the table." should read --In the table,--;
Column 13, line 25, "Corporation." should read --Corporation,--;
Column 15, line 67, "5.000 to about 35.000" should read --5,000 to about 35,000--;
Column 16, line 31, "5.000" should read --5,000--;
Column 17, line 4, "5.000" should read --5,000--.

Signed and Sealed this

Twenty-sixth Day of August, 1997

Attest:

BRUCE LEHMAN

*Attesting Officer*   Commissioner of Patents and Trademarks